United States Patent
Martin et al.

(10) Patent No.: US 8,144,951 B2
(45) Date of Patent: Mar. 27, 2012

(54) METHOD FOR DATA EVALUATION (75) Inventors: Diana Martin, Herzogenaurach (DE); Kirstin Jattke, Erlangen (DE); Horst Winder, Marloffstein (DE)

(73) Assignee: Siemens Aktiengesellschaft, Munich (DE)

( * ) Notice: Subject to any disclaimer, the term of this patent is extended or adjusted under 35 U.S.C. 154(b) by 978 days.

(21) Appl. No.: 12/153,556

(22) Filed: May 21, 2008

(65) Prior Publication Data
US 2008/0298664 A1 Dec. 4, 2008

(30) Foreign Application Priority Data
May 22, 2007 (DE) .......... 10 2007 023 656

(51) Int. Cl.
*G06K 9/00* (2006.01)
(52) U.S. Cl. ........ 382/128
(58) Field of Classification Search ........ 382/128
See application file for complete search history.

(56) References Cited

U.S. PATENT DOCUMENTS

| | | | |
|---|---|---|---|
| 7,848,553 B2 * | 12/2010 | Hertel et al. | 382/128 |
| 2005/0031176 A1 * | 2/2005 | Hertel et al. | 382/128 |
| 2006/0004275 A1 | 1/2006 | Vija et al. | |
| 2006/0052685 A1 | 3/2006 | Cho et al. | |
| 2007/0102641 A1 | 5/2007 | Schmand et al. | |
| 2007/0242069 A1 * | 10/2007 | Matsue et al. | 345/428 |
| 2008/0043901 A1 * | 2/2008 | Maschke | 378/4 |
| 2008/0064949 A1 * | 3/2008 | Hertel et al. | 600/407 |
| 2008/0181472 A1 * | 7/2008 | Doi et al. | 382/128 |
| 2008/0199059 A1 * | 8/2008 | Eck et al. | 382/128 |

FOREIGN PATENT DOCUMENTS
DE 10 2005 041 381 3/2006

OTHER PUBLICATIONS

Slomka, Software Approach to Merging Molecular with Anatomic Information, The Journal of Nuclear Medicine, vol. 45, No. 1, (Suppl), Jan. 2004.*
German Office Action issued Mar. 4, 2008.

* cited by examiner

*Primary Examiner* — Rodney Fuller
(74) *Attorney, Agent, or Firm* — Harness, Dickey & Pierce, P.L.C.

(57) ABSTRACT

A method for data evaluation of first and second measured data records acquired substantially simultaneously with the aid of a combined medical examination device suitable for simultaneous and isocentric acquisition of first measured data, includes reconstructing a first image data record from the measured data of the at least one first measured data record, reconstructing a second image data record from the measured data of the at least one second measured data record, fusing the image data records as a function of registering the coordinate systems of the first measured data record and of the second measured data record to form a fusion image data record, and displaying and/or storing the fusion image data record.

33 Claims, 4 Drawing Sheets

METHOD FOR DATA EVALUATION

PRIORITY STATEMENT

The present application hereby claims priority under 35 U.S.C. §119 on German patent application number DE 10 2007 023 656.7 filed May 22, 2007, the entire contents of which is hereby incorporated herein by reference.

FIELD

Embodiments of the invention generally relate to a method for data evaluation of first and second measured data records. For example, embodiments may relate to a method for data evaluation of first and second measured data records acquired substantially simultaneously with the aid of a combined medical examination device suitable for simultaneous and isoceritric acquisition of first measured data, specifically magnetic resonance or computed tomography measured data, and second nuclear medicine measured data, specifically PET measured data or SPECT measured data.

BACKGROUND

Particularly in order to examine functional processes, images recorded with the aid of different modalities, in particular images of a highly resolving modality and of a correspondingly sensitive modality, are frequently observed jointly in the course of an examination. There have been developed to this end so-called hybrid modalities that combine a modality having a high spatial resolution, for example magnetic resonance (MR) or computed tomography (CT) with a modality having a high sensitivity (nuclear medicine, for example PET (Positron Emission Tomography) or SPECT (Single Photon Emission Computed Tomography)). Some of these machines permit the simultaneous and isocentric imaging of the examination volume.

The combination of two modalities in one machine gives rise to an examination of enormous data volumes that must be assessed for making the diagnosis. To this end, data from hybrid systems are frequently viewed in a superposed display, as fused images.

In a method known for this purpose, image data records from various modalities are evaluated with the aid of manual post-processing functions. Respectively suitable image data records of the same anatomy are loaded into an application and visualized there in superposed fashion, whereupon a user can compile a fusion image manually. Such a procedure is, however, prone to error as well as being labor intensive and time consuming.

SUMMARY

In at least one embodiment of the invention, a method improved with regard thereto is specified.

In at least one embodiment, the method includes:
reconstructing a first image data record from the measured data of the at least one first measured data record,
reconstructing a second image data record from the measured data of the at least one second measured data record,
fusing the image data records as a function of registering the coordinate systems of the first measured data record and of the second measured data record to form a fusion image data record, and
displaying and/or storing the fusion image data record.

In at least one embodiment, the invention uses the fact that a simultaneous and isocentric acquisition of measured data is possible in order to generate an appropriate fusion image data record in an automated fashion after an appropriate reconstruction of the image data. This is possible owing to the isocentric design of the combined medical examination device, and also owing to the fixed relationship of the measurement coordinate systems to one another. The registration required for superpositioning can already be permanently prescribed by the geometric conditions, but can also easily be determined in the course of a calibration measurement. Since even a modern examination device is subject to mechanical changes over time, it can be sensible to check the calibration regularly.

The first step in at least one embodiment of the inventive method is to reconstruct image data records from the raw measured data. For example, it is also possible in such a step to combine a number of two-dimensional tomograms to form a three-dimensional reconstruction image data record, for example in the case of magnetic resonance. In the case of CT as well, the recorded two-dimensional X-ray images are merged to form a three-dimensional image data record.

Since the relationship of the coordinate systems of the first image data records (magnetic resonance or computed tomography measured data record) and second image data records (nuclear medicine image data records) thus obtained is known, the first image data record and the second image data record can be combined to form a fusion image data record. The latter is then either displayed and/or stored for later analysis.

The fusion, in particular also the superposition, of the data records can take place very simply and therefore without a large time outlay in the case of simultaneous isocentric measurements. The step of coregistering the image data records with the aid of user interaction, which is labor intensive and time consuming and prone to error, is advantageously eliminated, and so it is, in particular, also possible to have recourse to fused image material more quickly in the case of time critical applications. In addition, the fusion carried out with the aid of the automatic method of the present invention is more exact and permits a diagnosis that is less prone to error.

In particular, in accordance with at least one embodiment of the inventive method the reconstruction and fusion taking place in real time can also be used as a fast basis for deciding whether the data quality is adequate and whether further measures are required. In this way, at least one embodiment of the invention simplifies and accelerates the evaluation of measured data acquired in a hybrid modality.

It is possible for the first time in conjunction with the hybrid modalities mentioned here to carry out registration and image fusion in a fully automatic fashion. Present day methods always require the operator to intervene. Since there is no "mechanical" coregistration, the operator must always at least confirm the registration in the case of fused data records (even make manual corrections in many cases or operate entirely manually). Only by virtue of the simultaneous, isocentric acquisition in described systems is it possible to carry out the registration automatically, that is to say without user interaction and immediately, and thus in the environment of the data reconstruction. The system intrinsically ensures the stationaryness, and can also determine the time correlation. Data records that have been acquired simultaneously can be fused without user interaction. Data records from different time windows can be brought into the correct position before fusion with the aid of suitable movement correction methods. It is only in this set up that all the parameters permitting automated fusion are present in at least one embodiment of the system.

In order to accelerate at least one embodiment of the method, it is possible, for example, to provide that the first image data record and the second image data record are reconstructed in time parallel fashion. Here, it may only be ensured that all the information for image reconstruction is present.

At least one embodiment of the inventive method can expediently be executed in parallel with further recording processes. If, for example, entire image series are recorded, it is possible while the acquisition of further measured data is still running for a reconstruction and fusing of the previously acquired measured data already to take place, and it may also be possible to use said measured data in order to plan the further procedure.

In such a case, when acquisition and at least one embodiment of the inventive method, that is to say the evaluation, run in parallel, it can also be provided in order to optimize the timings that the fusing is carried out during the reconstruction of further image data records to be fused. Thus, while the next image data records are already being reconstructed the image data records just reconstructed are further fused. In this way, the evaluation process can be extremely accelerated and the fusion image data records can be obtained virtually in real time.

It can be provided with particular advantage that information obtained from the first or the second measured data record is taken into account for reconstructing the second or first image data record, the reconstruction of this second or first image data record being postponed until information is present. For example, it is usual to determine movement corrections in the case of magnetic resonance pictures. These movement corrections can also be applied to nuclear medicine measured data, for example PET measured data. In this case, the image reconstruction from the second measured data record is postponed until the movement correction data are present.

If a number of first or second image data records to be fused are present, fusion of each individual pair of first or second image data records can take place or, alternatively, a number of image data records can be reconstructed to form a single first or second image data record that is fused with the second or first image data record. A number of first measured data records will frequently be present, since the acquisition times for nuclear medicine pictures mostly exceed those of the magnetic resonance or CT pictures. The time frame for magnetic resonance pictures is, for example, in the range of seconds, but that for PET pictures is in the range of minutes.

In a particularly advantageous refinement of at least one embodiment of the invention, it can be provided that at least two first and/or at least two second measured data records acquired in conjunction with various imaging parameters are reconstructed to form at least two first and/or second image data records, all the first and second image data records being fused to form the fusion image data record. A number of instances are conceivable in this case. Thus, it is possible to provide whole body or partial body pictures that are carried out in a number of steps. In this process, the corresponding image data records can both be assembled over the entire anatomy and fused. This results both in whole body or partial body image data records of the individual modalities, and in a whole body or partial body fusion image data record.

In another example embodiment, both functional and anatomical magnetic resonance pictures can be present as first measured data. In this case, as well, a fusion of the two first image data records with the second image data record can take place such that the fusion image data record contains anatomical magnetic resonance information, functional magnetic resonance information and the nuclear medicine information.

Of course, the reconstruction and the fusion need not take place according to a permanently prescribed scheme, but rather reconstruction and/or parameters controlling the fusing can be used, in particular, as part of a measurement protocol. Such parameters can, for example, comprise an intensity weighting and/or a contrast and/or an opacity factor and/or a subvolume of interest and/or parameters relating to an automatic segmentation. In this case, standard values can be prescribed at least partially for the parameters. It can likewise be prescribed that the parameters are input at least partially by a user. However, it is expediently provided that the parameters are automatically determined at least partially from recording specific and/or examination specific and/or patient specific and/or doctor specific data, in particular a measurement protocol and/or an electronic patient file. Consequently, use is made of information that is either internally present in any case for the examination device, for example on the basis of the measurement protocol, or can be determined from external sources such as an electronic patient file. For example, data delimiting the target zone can be taken over from an electronic patient file such that the reconstruction and/or fusion takes place only in this target volume. The imaging parameters of a measurement protocol can be used to infer which resolution and intensity or which contrast are required. These inputs need then no longer be undertaken by a user in fashion prone to error, but the values can be determined automatically by the system. It is also conceivable that doctor specific or patient specific parameters be stored in the manner of a user profile and can be used in at least one embodiment of the method.

In addition to resorting to parameters, also conceivable independently thereof is a refinement in which regression data from preceding examinations are taken into account during fusion in order to mark specific features in the fusion image data record. Such regression data can also originate from patient files and, for example, comprise striking features that have been determined in preceding experiments. These already detected striking features can be specially marked in the fusion image, for example by an additional mark such as a frame or an arrow with text. However, it can also expediently be provided that marked features are displayed with colored markings. Thus, for example, problem zones already detected can be displayed in red in order to direct the doctor's view more quickly to these relevant zones.

When use is made of a three-dimensional first and second image data record, it can be provided that at least one two-dimensional sectional image data record is reconstructed in a further step from the three-dimensional fusion image data record. For example, orthogonal central sections can be produced in this way. It is also possible to implement a successive two-dimensional display of the examination zone in this way.

It can, however, also happen that the first or the second image data record is only two-dimensional, for example that only a sectional image is recorded. When use is made of a three-dimensional or a two-dimensional image data record, it can therefore be provided that fusion takes place in the region covered by the two-dimensional image data record in order to form a two-dimensional fusion image data record. Alternatively, it can also be provided that the two-dimensional image data record is placed in the three-dimensional image data record in an appropriately marked fashion.

As already mentioned, at least one embodiment of the method can be carried out virtually in real time because of the advantageous use of the medical examination device, which is designed for the simultaneous and isocentric acquisition of the measured data of both modalities. This is of use, in particular, when an examination is being carried out in which the measured data are completed or updated in sequential steps by way of further recordings. In such a case, it can be provided with particular advantage that given the presence of a more current first and/or second measured data record, the more current first and/or second measured data record is reconstructed to form a more current first and/or second image data record, after which a more current fusion image data record is determined by renewed fusing of the first image data record with the second image data record, and displayed and/or stored.

In such multistep methods, it is therefore possible to use at least one embodiment of the inventive method to perform a real-time image reconstruction, a real-time superposition and a real-time display. For example, a fast magnetic resonance measurement can be performed in the case of a combined MR/PET examination, the PET measured data being automatically reconstructed starting from a specific threshold value. However, PET measured data continue to be acquired and to be repeatedly renewed. An ever improving PET measured data record thereby results. This measured data record can be reconstructed with each updating, or regularly, to form a PET image data record, and be superposed on the magnetic resonance image data record such that a current fusion image data record results. A user is, for example, capable of detecting therefrom whether an adequate data quality has already been achieved and, in particular also of ending the acquisition.

However, the acquisition can also be appropriately adapted in the case of such real-time procedures. If, for example, the user detects that specific regions need to be acquired more accurately, he can make this decision on the basis of the fusion image data already conditioned and displayed or capable of being displayed.

A common computing device, for example, the control device of the examination device, can advantageously be used to carry out at least one embodiment of the method. It has previously been customary to carry out the reconstruction and fusion on different computing devices. The material outlay required therefore is lowered with the aid of at least one embodiment of the inventive method such that a more cost effective solution results. In particular, however, the use of a common computing device can yield an improved synchronization, for example with reference to the queue and the queue mechanisms. The reconstruction and the fusion can be performed in a fashion perfectly attuned to one another. For example, in the case of functional brain examinations that are frequently also carried out with a combination of magnetic resonance and PET, an improved synchronization is extremely helpful because various activity states of the brain are distinguished in appropriate time windows, the respective time windows being intended to be handled jointly.

The fusion image data record can be stored as a DICOM file, in particular as a DICOM Secondary Capture Object and/or as a DICOM Spatial Registration Object, and/or in a proprietary format. A DICOM Secondary Capture Object can be interpreted by most work stations, but leaves only a short margin for further processing. A DICOM Spatial Registration Object, frequently used in conjunction with hanging protocols, constitutes a more recent standard and can be interpreted only by a few work stations or archive systems. This file format essentially regulates the superposed display of the original image data records.

In particular, it can also be provided that the fusion image data record is stored in the format of the first image data record. For example, the fusion image data can be stored in the format of a magnetic resonance image data record. It can expediently be provided that the second image data record can be back-calculated from the fusion image data record. For example, PET image data can be back-calculated from the magnetic resonance image data.

Particularly when use is made of a proprietary image format, it can be provided with particular advantage that fusion parameters are stored with the fusion image data record, and the fusion image data record is adapted in the event of subsequent change. It is then also subsequently still possible to access the first and second image data records, whereupon a new fusion can take place by taking account of the change after a subsequent setting of the superposition parameters.

It can expediently be provided that the fusion image data record is displayed in common with the first and the second image data record. For example, the first image data record can be displayed on the right, the second image data record on the left, and the superposition composed of the first and the second image data record in the middle.

The display of the fusion image data record can preferably take place such that through color coding of the first and the second image data record, in particular, the image data of the first and the second image data record can be distinguished by the viewer. Such a visualization can take place, for example, by way of suitable color tables. The viewer is still able in this way to assign the individual image data records.

In addition to the method, at least one embodiment of the invention also relates to a combined medical examination device having a control device that is designed to execute at least one embodiment of the inventive method. Such a medical examination device then has a first imaging modality, specifically a magnetic resonance or computed tomography device, and a second imaging modality, specifically a PET device or a SPECT device. Measured data acquired by the imaging modalities can be fed to the control device, and there be combined in accordance with at least one embodiment of the inventive method to form a fusion image data record, as well as be displayed and/or stored.

BRIEF DESCRIPTION OF THE DRAWINGS

Further advantages and details of the present invention emerge from the exemplary embodiments described below, as well as with the aid of the drawings, in which.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Figure 1:
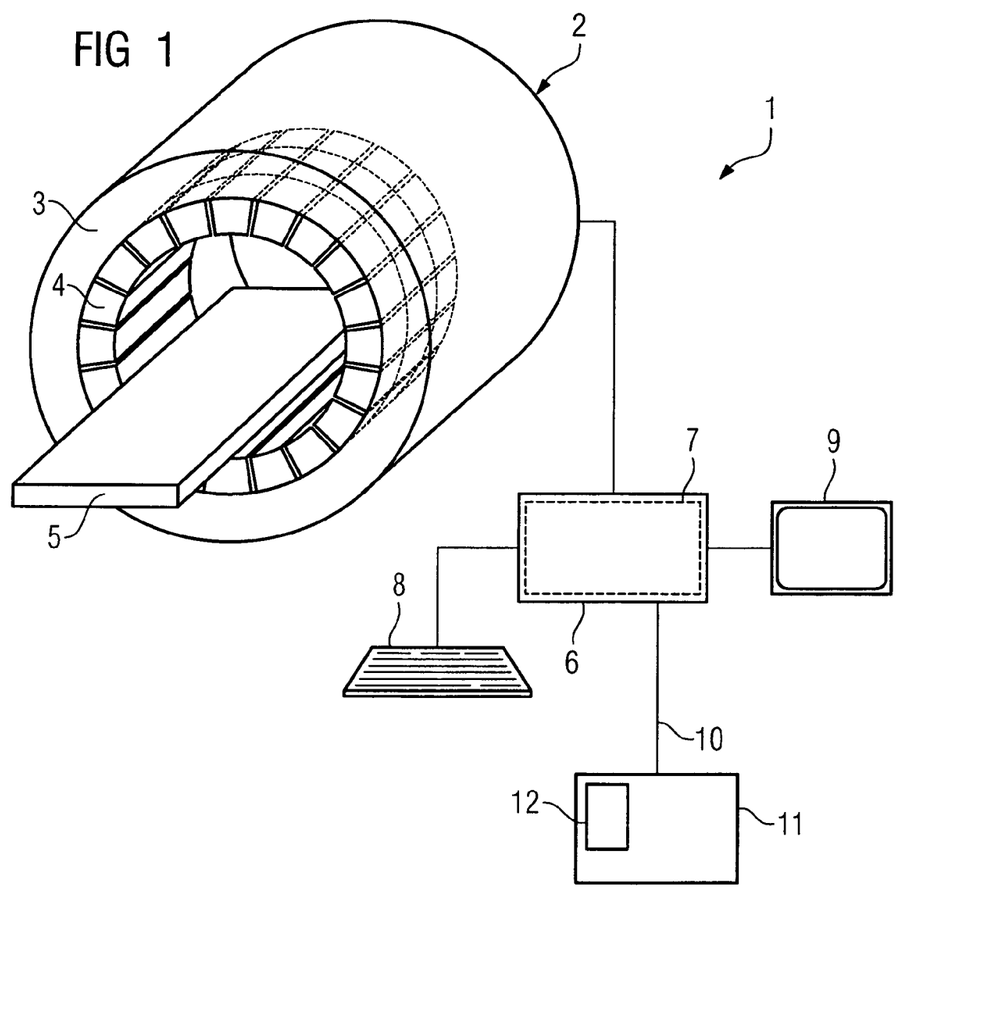
FIG. 1 shows an embodiment of an inventive medical examination device.

FIG. 1 shows the schematic sketch of an embodiment of an inventive medical examination device 1. It includes a combined magnetic resonance PET machine 2 that comprises a solenoid magnet 3 and gradient coils and radiofrequency coils (not shown in more detail) for acquiring magnetic resonance measured data as first measured data. A PET detector 4 for acquiring PET measured data as second measured data is provided inside the magnet 3. The magnet 3 and the PET detector 4 define a patient opening into which a patient can be moved on a patient couch 5 in order, for example, to be able to undertake a functional brain examination.

The medical examination device 1 further includes a control device 6 that can include a computing device 7. The control device 6 controls the acquisition mode and the evaluation mode of the machine 2. Connected to the control device 6 is an input device 8, for example a keyboard, and a monitor 9. By way of example, parameters for recording, in particular a measurement protocol, and for evaluating, in particular reconstruction and fusion parameters, can be input and varied via the input means 8. Further relevant data for the acquisition mode and evaluation mode can be supplied via a communication link 10 by external computing devices 11 on which, for example, an electronic patient file 12 is stored.

The control device 6 is designed to carry out an embodiment of the inventive method.

The medical examination device 1 contains with the combined MR/PET machine 2 only one example of a hybrid modality. The combinations PET/CT, SPECT/CT, MR/SPECT and others, for example, are also conceivable.

The medical examination device 1 can be used to acquire magnetic resonance and PET measured data isocentrically and simultaneously. The magnetic resonance data in this case constitute first measured data in the meaning of the present method, while the PET measured data constitute second measured data.

Figure 2:
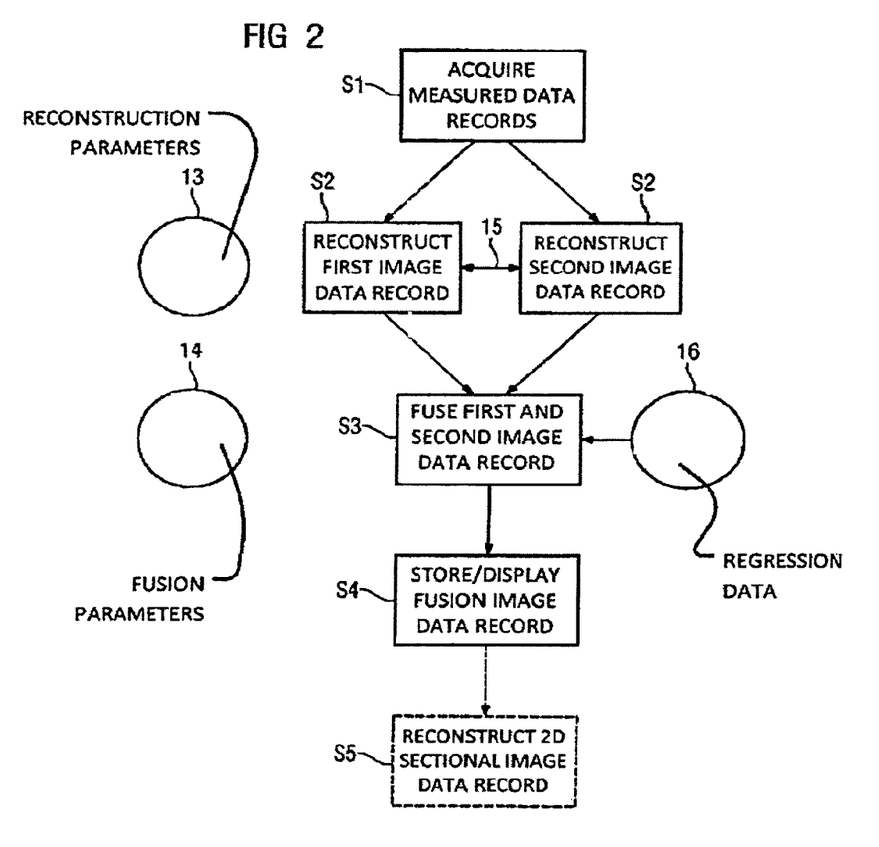
FIG. 2 shows a flowchart of an embodiment of the inventive method.

A possible sequence of an embodiment of the inventive method is illustrated in FIG. 2. Firstly, measured data records are acquired in a step S1. This usually takes place by way of a so-called measurement protocol in which it is also already possible to store reconstruction parameters 13 and fusion parameters 14 for the subsequent data evaluation. The results of the acquisition process are at least a first measured data record, a magnetic resonance measured data record in the example, and at least a second measured data record, a PET measured data record in the example. It is possible in the inventive method to reconstruct—step S2—a first and a second image data record from the first and the second measured data record in a parallel fashion, that is to say substantially simultaneously.

It may be remarked at this juncture that an embodiment of the inventive method can be executed in principle in a fashion parallel to exemplary further acquisition processes. A real-time data evaluation is thereby achieved in addition to the acquisition mode. In particular, it is even possible for a number of method steps of various instances of method to run parallel to one another. Thus, it is conceivable for first and second image data records already to be reconstructed (step S2) during the fusing of the image data records that takes place in step S3.

In addition, in the case of an embodiment of the inventive method it is possible to take account of information obtained from the first or the second measured data record for the purpose of reconstructing the second or first image data record, the reconstruction of the second or first image data record being postponed until the information is present. If, for example, information relating to the movement correction is derived from magnetic resonance measured data, the reconstruction of a PET measured data record can be postponed until this information is present and the movement correction can also be applied in the case of the PET measured data record. This information transfer is symbolized by the arrow 15.

The reconstruction of the image data records takes place according to generally known methods, and corresponds to the special requirements placed on the respective modality. The reconstruction includes both the fundamental conversion of the measured data into images and, if appropriate, the combination of sectional images or 2D images recorded at various angles to form a three-dimensional image data record. The reconstruction parameters 13, which, like the fusion parameters 14, have been input by a user, prescribed in standard terms, or else automatically determined from other information such as, for example, recording specific and/or examination specific and/or patient specific and/or doctor specific data, determine the precise sequence of the reconstruction. The result of the reconstruction in steps S3 is at least a first and at least a second image data record. Following thereupon is the fusion of the image data records to form a fusion image data record, step S3, while taking note of the fusion parameters 14.

It is possible in the process to distinguish some cases in an embodiment of the inventive method when a number of first or second measured data records are present. If, for example, a number of first and/or second image data records to be fused are present, for example in the case of magnetic resonance pictures that take place relatively quickly, by comparison with PET pictures, which take place slowly, it can be provided that each individual pair of first and second image data records is fused to form a dedicated fusion image data record.

Alternatively, however, it can also be provided that the several measured data records are reconstructed to form a single first and/or second image data record such that only the reconstruction of a first with a second image data record to form a fusion image data record takes place. This can make sense, for example, whenever the aim is to average statistically over a number of measured data records. The further reaching the averaging, the steeper the rise in data quality, assuming that they are acquired under the same circumstances. This is important in particular for functional brain pictures.

However, it is also conceivable that a number of first and/or second measured data records are acquired for various imaging parameters. For example, functional and anatomical magnetic resonance pictures can be available that are present as two different first image data records. It can then also be provided that the measured data records are reconstructed to form various first image data records, more than two image data records then being fused to form the fusion image data record.

The fusion, in particular the displacement, of the first and second image data records in step S3 is enabled by a known registration of the coordinate systems of the first and the second measured data record. A fixed relationship between the measurement coordinate systems is given by the geometry permanently prescribed, for example, in the combined magnetic resonance PET machine 2. This relationship can be determined by a calibration measurement and, if appropriate, be checked at regular time intervals. If appropriate, however, it can also be derived from the geometric conditions without a calibration measurement. It is now possible to compile the fusion image data record on the basis of this registration.

However, it is also possible in the case of an embodiment of the inventive method to take account of regression data 16 from preceding examinations during fusing. Specific features can then be marked in the fusion image data record, for example in color. Such features can, for example, be striking features or diagnostic findings. Regression data 16 can, for example, be obtained from an electronic patient file 12. The regression data 16 can originate with particular advantage from examinations that were carried out using the same medical examination device 1. There is then no need for any further registration or even a search for specific anatomical features, but instead the regression data can be taken into account directly. This is advantageous in the case of follow-up investigations, in particular.

Various possibilities are to be borne in mind in the fusion. If the first and the second image data record are respectively three-dimensional, a three-dimensional fusion image data record is also determined. If, however, one of the image data records is only two-dimensional, a fusion can take place only in the region covered by the two-dimensional image data record (for example a tomogram), such that a two-dimensional fusion image data record results. Alternatively, it is also conceivable, of course, to place the two-dimensional image data record in the three-dimensional image data record such that a three-dimensional fusion image data record results nevertheless.

The fusion image data record is then stored or displayed, for example on the monitor 9, in step S4. Storage can take place, for example, as a DICOM file and/or in a proprietary format. "DICOM Secondary Capture Object" or "DICOM Spatial Registration Object" can be used, for example, as file format. The advantage of a proprietary format, as is described further later, is that it is also possible to store the fusion parameters 14, as well, and that subsequent allocation of the fusion can be undertaken.

If a three-dimensional fusion image data record results, it is possible to provide a further step S5, represented here only by dashes because of its optional nature, in which at least one two-dimensional sectional image data record is reconstructed from the three-dimensional fusion image data record. For example, it is possible to produce an orthogonal central section, or a series of two-dimensional sectional images that can be displayed one after another. Step S5 can, of course, also take place before step S4.

It still remains in general to remark that carrying out an embodiment of the method requires only the control device 6 or its computing device 7. Consequently, on the one hand further hardware is saved, while on the other hand a further synchronization of the data processing is also possible. This is sensible particularly in the case of examinations where synchronicity is important, for example in the case of functional brain examinations. In particular, it is also possible to undertake parallel processing of the data, especially in a fusion step and in filter steps or the like.

An intensity weighting and/or a contrast and/or an opacity factor and/or a subvolume of interest and/or parameters relating to an automatic segmentation may be named as examples of the reconstruction parameters 13 and the fusion parameters 14.

Figure 3:
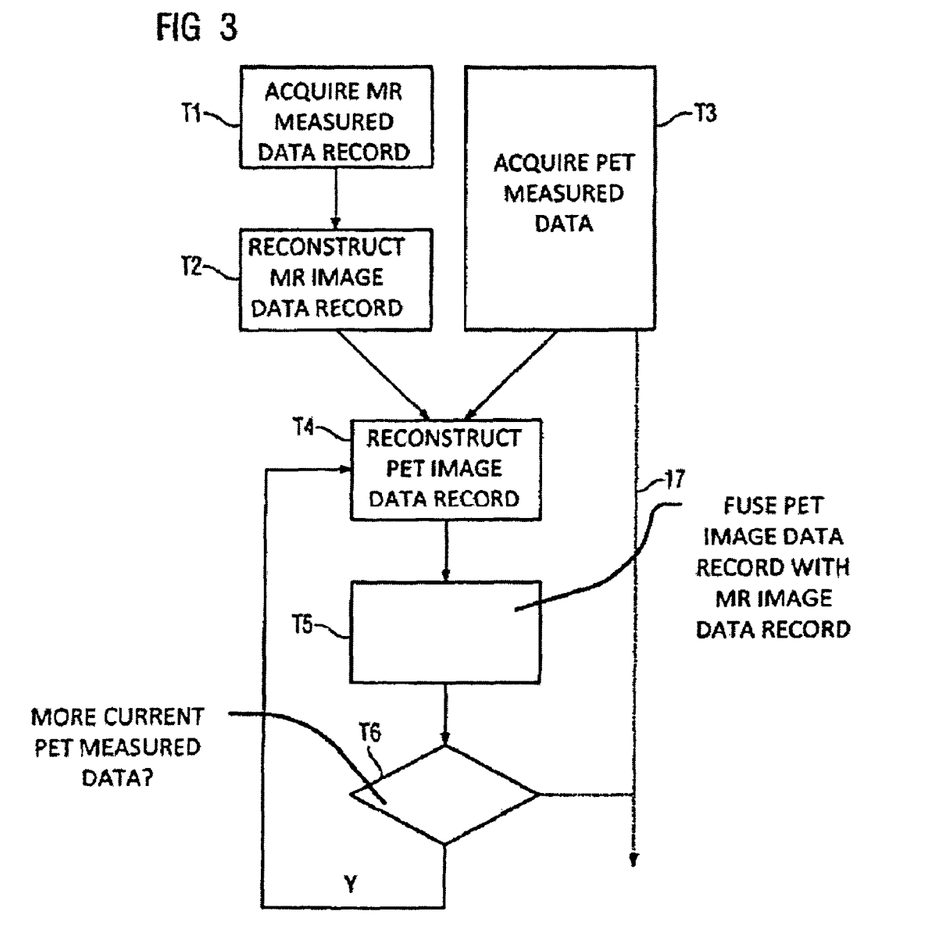
FIG. 3 shows a flowchart of the inventive method in a particular embodiment.

FIG. 3 shows a special, particular embodiment of the inventive method relating to the way in which the latter can be carried out within the medical examination device 1. In particular, a part of the method is repeated in this case iteratively for the purpose of updating.

A magnetic resonance measured data record is acquired in a step T1. This can take place much more quickly than the acquisition of PET measured data, since the acquisition of a magnetic resonance measured data record lasts seconds, while that of a PET measured data record mostly lasts minutes. Hereafter, a magnetic resonance image data record is reconstructed therefrom in a step T2. The steps T1 and T2 can be repeated at regular intervals in order to collect movement correction information relating to the time of the acquisition of the PET measured data, which, always takes place in parallel in step T3. As indicated by the dotted arrow 17, the acquisition of PET measured data takes place during the entire time, but can be interrupted, for example when PET tracer has subsequently to be injected, or activation must be renewed.

Once sufficient PET measured data are collected in order to obtain a PET measured data record, it is also possible to reconstruct a PET measured data in a step T4 in order to form a PET image data record. This can also feature, in particular, movement correction information from steps T1 and T2. In step T5, there is in turn the fusion of the PET image data record and the MR image data record to form a fusion image data record, and the fusion image data record is displayed and stored.

In a step T6, a check is then carried out as to whether in the meantime there are present sufficient more current PET measured data that result in a more current PET measured data record of better quality together with the PET measured data previously taken into account. If this is the case, the current PET measured data record is reconstructed in turn in step T4 to form a PET image data record. After the fusion to form a more current fusion image data record has taken place in step T5, said fusion image data record can also be displayed such that a user can directly assess to what extent enough data have already been collected, or whether the data quality is high enough. In particular, it is then also possible to change recording parameters. The user is therefore always informed of the current data situation.

Figure 4:
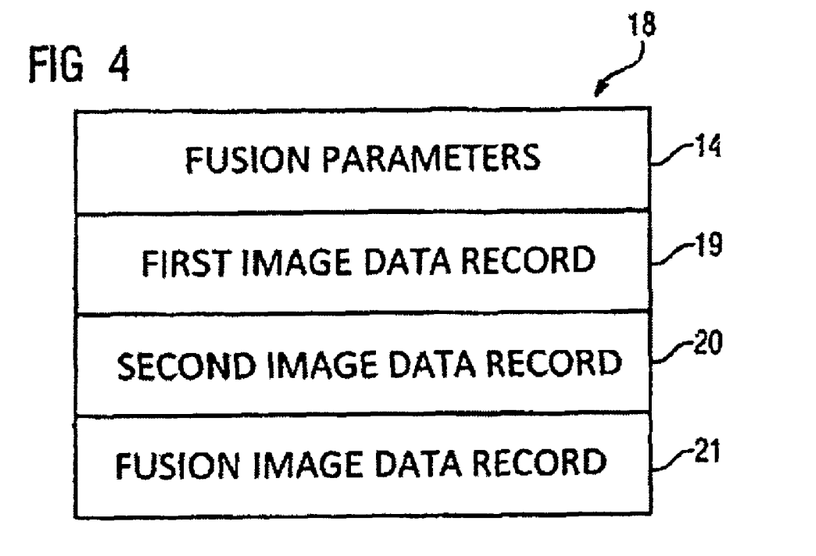
FIG. 4 shows a possible proprietary file format.

FIG. 4 shows an example of a proprietary file format 18 in which the fusion image data record can be stored. Such a file 18 initially contains the fusion parameters 14. These can also too be subsequently changed, since the first and the second image data record 19, 20 are also still stored in the file 18. The fusion image data record 21 can also be stored in the file. If the first and the second image data record 19 and 20 can, however, be back-calculated in any case from the fusion image data record 21, there is, of course, no longer a need for these to be stored separately.

It is advantageously possible still to undertake a change subsequently owing to the storage of the fusion parameters with the image data records. This is frequently impossible in the case of DICOM formats.

Figure 5:
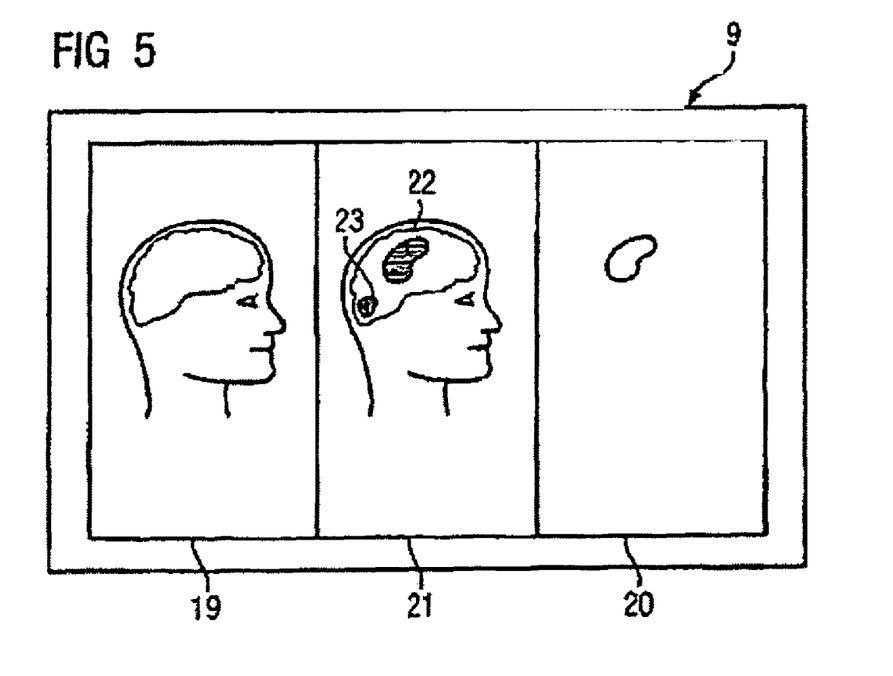
FIG. 5 shows a possible display of the fusion image data record with the first and the second image data record.

Finally, FIG. 5 shows a possibility of displaying the image data records on the monitor 9. In the example shown, an anatomical, first magnetic resonance image data record 19 is displayed on the left, while on the right a functional, second PET image data record 20, and in the middle the fusion image data record 21 are displayed. The image data 22 of the second image data record 20 are displayed therein in another color so that the viewer can distinguish them easily. Likewise displayed in the fusion image data record 21 is a striking feature 23 that is known from regression data 16. This, once again, is displayed in another color. In this way, the viewer obtains all the information relevant for a diagnosis.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDS; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for data evaluation of first and second measured data records acquired substantially simultaneously with the aid of a combined medical examination device suitable for simultaneous and isocentric acquisition of at least one first measured data and at least one second measured data, the method comprising:
reconstructing a first image data record from the at least one first measured data;
reconstructing a second image data record from the at least one second measured data;
fusing the reconstructed first and second image data records as a function of registering coordinate systems of the at least one first measured data record and of the second measured data record to form a fusion image data record; and
at least one of displaying and storing the fusion image data record: wherein given the presence of a number of first or second image data records to be fused,
fusion of each individual pair of first or second image data records takes place, or
a number of image data records are reconstructed to form a single first or second image data record that is fused with the second or first image data record.

2. The method as claimed in claim 1, wherein the first image data record and the second image data record are reconstructed in time parallel fashion.

3. The method as claimed in claim 2, wherein the method is executed in parallel with further recording processes.

4. The method as claimed in claim 1, wherein the method is executed in parallel with further recording processes.

5. The method as claimed in claim 1, wherein the fusing is carried out during the reconstruction of further image data records to be fused.

6. The method as claimed in claim 1, wherein at least one of reconstruction and parameters controlling the fusing are used.

7. The method as claimed in claim 6, wherein standard values are prescribed at least partially for the parameters.

8. The method as claimed in claim 6, wherein the parameters are input at least partially by a user.

9. The method as claimed in claim 6, wherein the parameters are automatically determined at least partially from recording at least one of specific, examination specific, patient specific and doctor specific data.

10. The method as claimed in claim 6, wherein the parameters comprise parameters relating to at least one of an intensity weighting, a contrast, an opacity factor, a subvolume of interest, and an automatic segmentation.

11. The method as claimed in claim 10, wherein marked features are displayed with colored markings.

12. The method as claimed in claim 6, wherein at least one of reconstruction and parameters controlling the fusing are used as part of a measurement protocol.

13. The method as claimed in claim 1, wherein a computing device is used to carry out the method.

14. The method as claimed in claim 1, wherein the fusion image data record is stored as a DICOM file.

15. The method as claimed in claim 14, wherein the fusion image data record is stored at least one of as a DICOM Secondary Capture Object, as a DICOM Spatial Registration Object, and in a proprietary format.

16. The method as claimed in claim 1, wherein the fusion image data record is stored in the format of the first image data record.

17. The method as claimed in claim 16, wherein the second image data record is back-calculated from the fusion image data record.

18. The method as claimed in claim 1, wherein the fusion image data record is displayed in common with the first and the second image data record.

19. The method as claimed in claim 1, wherein the fusion image data record is displayed.

20. The method as claimed in claim 19, wherein the fusion image data record is displayed, such that through color coding of the first and the second image data record, the image data of the first and the second image data record are distinguishable by the viewer.

21. A combined medical examination device comprising: a control device, designed to execute the method as claimed in claim 1.

22. The method of claim 1, wherein the at least one first measured data includes at least one of magnetic resonance and computed tomography measured data, and wherein the at least one second measured data includes at least one of specifically PET measured data and SPECT measured data.

23. A tangible computer readable medium including program segments for, when executed on a computer device, causing the computer device to implement the method of claim 1.

24. A method for data evaluation of first and second measured data records acquired substantially simultaneously with the aid of a combined medical examination device suitable for simultaneous and isocentric acquisition of at least one first measured data and at least one second measured data, the method comprising:
reconstructing a first image data record from the at least one first measured data;
reconstructing a second image data record from the at least one second measured data;
fusing the reconstructed first and second image data records as a function of registering coordinate systems of the at least one first measured data record and of the second measured data record to form a fusion image data record; and
at least one of displaying and storing the fusion image data record; wherein
information obtained from the first or the second measured data record is taken into account for reconstructing the second or first image data record, the reconstruction of this second or first image data record being postponed until information is present.

25. The method as claimed in claim 24, wherein, given the presence of a number of first or second image data records to be fused,
fusion of each individual pair of first or second image data records takes place, or
a number of image data records are reconstructed to form a single first or second image data record that is fused with the second or first image data record.

26. A method for data evaluation of first and second measured data records acquired substantially simultaneously with the aid of a combined medical examination device suitable for simultaneous and isocentric acquisition of at least one first measured data and at least one second measured data, the method comprising:
reconstructing a first image data record from the at least one first measured data;
reconstructing a second image data record from the at least one second measured data;
fusing the reconstructed first and second image data records as a function of registering coordinate systems of the at least one first measured data record and of the second measured data record to form a fusion image data record; and
at least one of displaying and storing the fusion image data record; wherein
at least one of at least two first and at least two second measured data records acquired in conjunction with various imaging parameters are reconstructed to form at least one of at least two first and second image data records, all the first and second image data records being fused to form the fusion image data record.

27. A method for data evaluation of first and second measured data records acquired substantially simultaneously with the aid of a combined medical examination device suitable for simultaneous and isocentric acquisition of at least one first measured data and at least one second measured data, the method comprising:
reconstructing a first image data record from the at least one first measured data;

reconstructing a second image data record from the at least one second measured data;

fusing the reconstructed first and second image data records as a function of registering coordinate systems of the at least one first measured data record and of the second measured data record to form a fusion image data record; and at least one of displaying and storing the fusion image data record; wherein regression data from preceding examinations are taken into account during fusion in order to mark specific features in the fusion image data record.

28. A method for data evaluation of first and second measured data records acquired substantially simultaneously with the aid of a combined medical examination device suitable for simultaneous and isocentric acquisition of at least one first measured data and at least one second measured data, the method comprising:

reconstructing a first image data record from the at least one first measured data;

reconstructing a second image data record from the at least one second measured data;

fusing the reconstructed first and second image data records as a function of registering coordinate systems of the at least one first measured data record and of the second measured data record to form a fusion image data record; and at least one of displaying and storing the fusion image data record; wherein when use is made of a three-dimensional first and second image data record, at least one two-dimensional sectional image data record is reconstructed in a further step from the three-dimensional fusion image data record.

29. A method for data evaluation of first and second measured data records acquired substantially simultaneously with the aid of a combined medical examination device suitable for simultaneous and isocentric acquisition of at least one first measured data and at least one second measured data, the method comprising:

reconstructing a first image data record from the at least one first measured data;

reconstructing a second image data record from the at least one second measured data;

fusing the reconstructed first and second image data records as a function of registering coordinate systems of the at least one first measured data record and of the second measured data record to form a fusion image data record; and at least one of displaying and storing the fusion image data record; wherein when use is made of a three-dimensional or a two-dimensional image data record, fusion takes place in the region covered by the two-dimensional image data record in order to form a two-dimensional fusion image data record.

30. A method for data evaluation of first and second measured data records acquired substantially simultaneously with the aid of a combined medical examination device suitable for simultaneous and isocentric acquisition of at least one first measured data and at least one second measured data, the method comprising:

reconstructing a first image data record from the at least one first measured data;

reconstructing a second image data record from the at least one second measured data;

fusing the reconstructed first and second image data records as a function of registering coordinate systems of the at least one first measured data record and of the second measured data record to form a fusion image data record; and at least one of displaying and storing the fusion image data record: wherein given the presence of a more current at least one of a first and second measured data record, the more current at least one of a first and second measured data record is reconstructed to form a more current at least one of a first and second image data record, after which a more current fusion image data record is determined by renewed fusing of the first image data record with the second image data record, and at least one of displayed and stored.

31. A method for data evaluation of first and second measured data records acquired substantially simultaneously with the aid of a combined medical examination device suitable for simultaneous and isocentric acquisition of at least one first measured data and at least one second measured data, the method comprising:

reconstructing a first image data record from the at least one first measured data;

reconstructing a second image data record from the at least one second measured data:

fusing the reconstructed first and second image data records as a function of registering coordinate systems of the at least one first measured data record and of the second measured data record to form a fusion image data record; and at least one of displaying and storing the fusion image data record; wherein at least one of reconstruction and parameters controlling the fusing are used, and the parameters are automatically determined at least partially from recording at least one of a measurement protocol and an electronic patient file.

32. A computing device including a processor, the computing device comprising:

means for reconstructing a first image data record from the at least one first measured data;

means for reconstructing a second image data record from the at least one second measured data;

means for fusing the reconstructed first and second image data records as a function of registering coordinate systems of the at least one first measured data record and of the second measured data record to form a fusion image data record; and means for at least one of displaying and storing the fusion image data record; wherein information obtained from the first or the second measured data record is taken into account for reconstructing the second or first image data record, the reconstruction of this second or first image data record being postponed until information is present.

33. A medical examination device comprising:
the computing device of claim 32.

* * * * *